US006204271B1

United States Patent
Fairbanks et al.

(10) Patent No.: US 6,204,271 B1
(45) Date of Patent: Mar. 20, 2001

(54) ANALGESIC COMPOSITION AND METHOD FOR USING SAME

(75) Inventors: Carolyn A. Fairbanks, Rochester; George L. Wilcox, Golden Valley, both of MN (US); Laura S. Stone, E. Richmondhill (CA); Kelley F. Kitto, Minneapolis, MN (US)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/152,342

(22) Filed: Sep. 14, 1998

Related U.S. Application Data

(60) Provisional application No. 60/058,954, filed on Sep. 16, 1997.

(51) Int. Cl.$^7$ ........................... A61K 31/506; A61K 9/08
(52) U.S. Cl. ............................................. 514/269; 514/810
(58) Field of Search ..................................... 514/256, 310, 514/816, 269

(56) References Cited

PUBLICATIONS

Ossipov et al, An Isobolographic Analysis of the Antinociceptive effect combinations of Clonidine and Opiates (IDS Citetion) p. 1107–1116, Mar. 1990.*
Armah et al, General Pharmacology of the Novel Centrally Acting Antihypertensive Agent Moxonidine–Arzreim–Pursch Drug Research vol. 38 #11 No. 10.*
Codd, E.E., Press, J.B., Raffa, R.B., "Alpha$_2$–Adrenoceptors vs. Imidazoline Receptors: Implications for $\alpha_2$–Mediated Analgesia and Other Non–Cardiovascular Therapeutic Uses". [Review], *Life Sciences*, 56 (1995) 63–74.
Goyagi, T., Nishikawa, T., "Oral Clonidine Premedication Enhances the Quality of Postoperative Analgesia by Intrathecal Morphine", *Anesthesia and Analgesia*, 82 (1996).
Hylden, J.L.K., Wilcox, G.L., "Intrathecal Substance P Elicits a Caudally–Directed Biting and Scratching Behavior in Mice". *Brain Research.*, 217 (1981) 212–215.
Hylden, J.L.K., Wilcox, G.L., "Pharmacological Characterization of Substance P–Induced Nociception in Mice: Modulation by Opioid and Noradrenergic Agonists at the Spinal Level". *The Journal of Pharmacology and Experimental Therapeutics*, 226 (1983) 398–404.
Omote, K., Kitahata, L.M., Collins, J.G., Nakatani, K., Nakagawa, I., "Interaction Between Opiate Subtype and Alpha–2 Adrenergic Agonists in Suppression of Noxiously Evoked Activity of WDR Neurons in the Spinal Dorsal Horn", *Anesthesiology*, 74 (1991) 737–743.

Ossipov, M., Harris, S., Lloyd, P., Messineo, E., "An Isobolographic Analysis of the Antinociceptive Effect of Systemically and Intrathecally Administered Combinations of Clonidine and Opiates", *The Journal of Pharmacology and Experimental Therapeutics*, 255 (1990) 1107–1116.
Ossipov, M.H., Lopez, Y., Bian, D., Nichols, M.L., Porreca, F., "Synergistic Antinociceptive Interactions of Morphine and Clonidine in Rats with Nerve–Ligation Injury", *Anesthesiology*, 86 (1997) 1–9.
Reddy, S.V.R., Maderdrut, J.L., Yaksh, T.L., "Spinal Cord Pharmacology of Adrenergic Agonist–Mediated Antinociception", *The Journal of Pharmacology and Experimental Therapeutics*, 213 (1980) 525–533.
Roerig, S., Lei, S., Kitto, K., Hylden, J.L.K., Wilcox, G.L., "Spinal Interactions Between Opioid and Noradrenergic Agonists in Mice: Multiplicitivity Involves δ and $\alpha_2$ Receptors", *Journal of Pharmacology and Experimental Therapeutics*, 262 (1992) 365–374.
Roerig, S.C., Fujimoto, J.M., "Multiplicative Interaction Between Intrathecally and Intracerebroventricularly Administered Mu Opioid Agonists But Limited Interactions Between Delta and Kappa Agonists for Antinociception in Mice", *Journal of Pharmacology and Experimental Therapeutics*, 249 (1989) 762–8.
Stone, L.S., MacMillan, L.B., Kitto, K.F., Limbird, L.E., Wilcox, G.L., "The $\alpha_{2a}$ Adrenergic Receptor Subtype Mediates Spinal Analgesia Evoked by $\alpha_2$ Agonists and is Necessary for Spinal Adrenergic–Opioid Synergy", *Journal of Neuroscience*, 17 (1997) 7157–7165.
Wilcox, G.L., Carlsson, K.H., Jochim, A., Jurna, I., "Mutual Potentiation of Antinociceptive Effects of Morphine and Clonidine in Rat Spinal Cord", *Brain Research*, 405 (1987) 84–93.
Fairbanks, C.A., and Wilcox, G.L. "Moxonidine, an Inidazoline Receptor ($I_1$)/Alpha 2C Adrenergic Receptor Selective Agonist, Produces Spinal Antinociceptive Synergy When Co–Administered with Morphine and Deltorphin II", Poster Abstract Distributed at the 1997 Annual Meeting of the American Pain Society, Oct. 23, 1997.

* cited by examiner

Primary Examiner—Peter F. Kulkosky
(74) Attorney, Agent, or Firm—Evenson, McKeown, Edwards & Lenahan, P.L.L.C.

(57) ABSTRACT

A pharmaceutical analgesic composition comprise an opioid analgesic agent and moxonidine as a non-opioid agent with analgesic activity. Administration of an opioid analgesic agent and moxonidine as a non-opioid agent produces analgesia in the treatment of pain in mammals.

6 Claims, No Drawings

ANALGESIC COMPOSITION AND METHOD FOR USING SAME

This application relies on the priority of provisional application Ser. No. 60/058,954 (filed on Sep. 16, 1997).

FIELD OF THE INVENTION

The present invention is directed to producing analgesia in the treatment of pain in larger mammals, in particular in humans, by co-administration of an opioid analgesic agent and of an analgesically active non-opioid agent, and to pharmaceutical analgesic compositions comprising an opioid analgesic agent and an analgesically active non-opioid agent.

BACKGROUND OF THE INVENTION

Opioid analgesics such as e.g. morphine are the most powerful analgesic drugs. The pain relieving activity of opioid analgesics includes a depressive effect on the central nervous system. The analgesic activity of opioid analgesics such as morphine and deltorphin II can be mediated via different opioid receptors, for example via receptors $\mu$-opioid and $\delta$-opioid receptors. Opioid analgesics are invaluable for the treatment of severe acute or chronic pain as, for example, may occur in bone degenerative diseases and cancer conditions. They are easy to administer and they provide effective pain relief in most patients. Due to the excellent overall tolerability of opioids the doses of morphine and other strong opioids can be increased to relatively high levels. Yet, in particular upon long term use, there is a development of unacceptable side effects.

These side effects include the development of physical dependence and tolerance, sedation, respiratory depression, hypotension, increase in cerebrospinal fluid pressure, nausea, vomiting and constipation. In some patients, particularly in the chronically ill, the opioid side effects make it impossible to continuously administer sufficiently high dosages to adequately control pain over the needed period of time. There are also some pain conditions that do not sufficiently respond to opioid pain treatment alone. Therefore, there is a constant need for improved opioid containing analgesic combinations with increased analgesic activity which comprise opioid and non-opioid analgesically active agents and which offer the possibility of reducing the opioid dose needed for efficient pain relief and thereby also reducing the opioid side effects that might result from the otherwise required higher dosages.

It is therefore an object of the present invention to provide an opioid containing analgesic composition having high analgesic potency and a reduced propensity for causing undesirable side effects.

It is also an object of the invention to provide a non-opioid substance with analgesic effects showing synergy with the analgesic activity of the opioid, and to provide analgesic compositions comprising an opioid analgesic agent, in particular morphine, and such a synergistically effective non-opioid analgesic agent which allows to reduce the amount of the opioid necessary to achieve effective pain treatment.

It is further an object of the invention to provide a method for producing opioid induced analgesia in larger mammals, in particularly in humans, whereby undesirable side effects of acute and chronic administration of strong opioids are reduced.

SUMMARY OF THE INVENTION

The present invention is directed to producing analgesia in larger mammals, in particular in humans, by co-administering synergistically effective amounts of (1) 4-chloro-5-[(4,5-dihydro-1H-imidazol-2-yl)-amino]-6-methoxy-2-methylpyrimidine (generic name: moxonidine) of formula I,

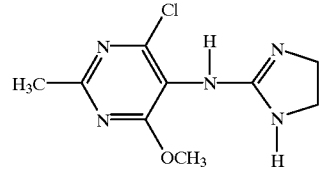

or its physiologically compatible acid-addition salts; and (2) of an opioid analgesic agent. The present invention further pertains to analgesic pharmaceutical compositions comprising synergestically effective amounts of moxonidine or its physiologically compatible acid addition salts and an opioid analgesic agent.

DETAILED DESCRIPTION OF THE INVENTION

According to the invention there is provided a pharmaceutical analgesic composition comprising synergistically effective amounts of (1) moxonidine or pharmaceutically acceptable salts thereof and of (2) an opioid analgesic agent or a pharmaceutically acceptable derivative or salt thereof. In such a combination the opioid agent or a pharmaceutically acceptable derivative or salt thereof can be administered in a low-analgesic dose, or even in a per se subanalgesic dose. The composition may contain both, moxonidine and the opioid agent, together in one dosage form or each in a separate dosage form.

Moxonidine and its pharmacologically acceptable salts used in accordance with the invention are within the scope of the 5-[(2-imidazolin-2-yl)-amino]-pyrimidine derivatives with blood pressure lowering properties described in the published German Patent Application No. 28 49 537, and are known from this patent application. Pharmaceutical preparations containing moxonidine are commercially available as antihypertensive medications under the trade name Physiotens®. The compounds can be manufactured in a known manner essentially in accordance with the processes described in the aforementioned published German Patent Application or in a manner similar to these processes. Moxonidine is known to be an imidazoline/$\alpha_2$-adrenergic ($I_1/\alpha_2$-AR) receptor agonist.

Salts with inorganic acids, such as hydrohalic acids, or with organic acids, for example lower aliphatic monocarboxylic or dicarboxylic acids such as acetic acid, fumaric acid or tartaric acid or aromatic carboxylic acids such as salicylic acid are suitable as physiologically compatible acid-addition salts of moxonidine.

It has now been found that moxonidine has an analgesic activity, which synergizes with the analgesic activity of opioids, in particular opioids such as morphine or deltorphin II, when moxonidine and such an opioid analgesic are co-administered for the treatment of pain. This co-administration results in a greater-than-additive effect (i.e., synergy).

The opioid agonist with opioid receptor activity used in the present invention may be selected from morphine and compounds structurally related to morphine, or functionally related to morphine such as deltorphin II, or pharmaceutically acceptable derivatives or salts thereof. Further examples of clinically opioid analgesics are e.g. fentanyl and remifentanil. Most preferably used is morphine. Suitable pharmaceutically acceptable salts of opioids include hydrochlorides, hydrobromides, hydroiodides, sulphates, bisulphates, nitrates, citrates, tartrates, bitartrates, phosphates, malates, maleates, fumarates, succinates, acetates, terephthalates, pamoates and pectinates. Preferably, the pharmaceutically acceptable salt of morphine is a hydrochloride, a sulphate or a tartrate.

The dosages of opioid compounds to be administered for the relief of pain naturally vary depending on the type and severeness of the condition to be treated, as well as on the type of the opioid compound and of the route of administration used. For example, dosages of 10 to 20 mg of morphine per single unit dosage form are common for liquid analgesic formulations. According to the invention, by administering a combination of an opioid with moxonidine, equal pain relieving effects may be achieved with dosages that are substantially reduced as compared to the dosages needed when the opioid is administered alone. Depending on the amount of moxonidine added, dosages may be reduced down to $\frac{1}{30}$, suitably down to $\frac{1}{6}$ to $\frac{1}{10}$. In order to provide a synergistic interaction according to the present invention, the quantitative ratio of moxonidine to the opioid is particularly chosen such that the weight-to-weight ratio of moxonidine to the opioid is such that the effective doses for each of the two compounds range from 25% to 75% ($ED_{25}$ to $ED_{75}$); in other words, the ratio of doses for 25% to 75% effect of each compound, when administered alone, may be used to set the ratio of moxonidine to the opioid to be administered in an individual dosage form. Preferably, the quantitative ratio of moxonidine to the opioid is chosen such that the contribution of analgesic efficacy from each, moxonidine and the opioid, is approximately in the same order (40–60%:60–40%), and in particular equal. For example, when equi-effective analgesic amounts of moxonidine and morphine are used in combination, an enhancement of the analgesic potency of morphine of up to about 6-fold of the theoretically expected additive potency is observed, and for moxonidine, respectively, an enhancement of up to about the 9-fold potency of the theoretically expected (additive) potency is found.

According to the invention analgesia is produced in larger mammals, in particular in humans, by administering to a patient in need of such treatment the respective amounts of moxonidine or a pharmaceutically acceptable salt thereof and of an opioid analgesic or a pharmaceutically acceptable derivative or salt thereof, in separate dosage forms or in a combined dosage form.

Any suitable route of administration may be employed. Intrathecal administration has proven to be most effective.

For example, according to the invention synergistically active quantities of the compounds that are used for the treatment and/or prophylaxis of pain can be contained together with customary pharmaceutical excipients and/or additives in solid or liquid pharmaceutical formulations. Examples of solid dosage forms are tablets, coated tablets, capsules, powders, granules or suppositories. These solid dosage forms can contain standard pharmaceutical inorganic and/or organic excipients such as lactose, talc or starch in addition to customary pharmaceutical additives such as lubricants or tablet disintegrants. Liquid preparations such as solutions, suspensions or emulsions of the active ingredients can contain the usual diluents such as water, oil and/or suspending aids such as polyethylene glycols and such like. Further additives such as preservatives and the like may also be added.

The active ingredients can be mixed and formulated with the pharmaceutical excipients and/or additives in a known manner. For the manufacture of solid dosage forms, for example, the active ingredients may be mixed with the excipients and/or additives in the usual manner and granulated in a wet or dry process. Granules or powder can be filled directly into capsules or compressed into tablet cores. If desired, these can be coated in a known manner. For the manufacture of liquid dosage forms the active compounds are dissolved or suspended in a suitable liquid carrier and optionally suitable adjuvants may be added.

Pharmaceutical compositions suitable for injection (i.e., spinal intrathecal administration) may be sterilised solutions containing an effective amount of the compounds used according to the invention dissolved in a physiologically acceptable isotonic saline solution (i.e., containing 0.9% by wt. sodium chloride). Usually these solutions are adopted in a known manner to the physiological characteristics of the site of administration.

The synergistic analgesic activity of combinations of moxonidine with opioids such as e.g. morphine and deltorphin II may be shown in pharmacological standard tests in mice, e.g., in the tail flick test and the substance P (SP) nociceptive test.

TESTS AND RESULTS

Experimental tests were carried out to show that moxonidine and opioids (e.g., morphine or deltorphin II), when adminstered simultaneously, are synergistically effective in inhibiting substance P-elicited nociceptive behaviour in ICR mice. Moxonidine, as well as morphine or deltorphin II alone each inhibited substance P-elicited nociceptive behaviour. $ED_{50}$ values were determined for each of these agents. Equi-effective doses of moxonidine and the opioid were used in the test combinations moxonidine/morphine and moxonidine/deltorphin II. The interactions of moxonidine and the respective opioid were determined by isobolographic analysis of the dose-response curves of moxonidine/morphine- and of moxonidine/deltorphin II-combinations containing equi-potent amounts of moxonidine and the opioid. The observed $ED_{50}$ values of the combinations were compared statistically against their respective calculated theoretical additive $ED_{50}$ values. The combinations of moxonidine/morphine and moxonidine/deltorphin II resulted in significant leftward shifts in the dose-response curves compared to those of each agonist administered separately. The $ED_{50}$ values of the dose response curves of these combinations were significantly less than the corresponding calculated theoretical additive $ED_{50}$ values. These results indicated that moxonidine is synergistically effective with both morphine or deltorphin II. Taken collectively, these data demonstrate that moxonidine combined with opioid agonists produces spinal analgesic synergy. Therefore, spinally administered moxonidine/opioid combinations provide an effective therapeutic strategy to manage pain.

List of Abbreviations:

AR: adrenergic receptors; $\alpha_2$ AR: alpha 2 adrenergic receptors; C.L.: Confidence Limits; δOR: delta opioid receptor; DELT II: deltorphin II; $ED_{50}$-value: effective dose 50%; $ED_{80}$ value: effective dose 80%; $ID_{50}$: inhibitory dose 50% value; $I_1$: imidazoline$_1$; i.p.: intraperitineal; IR: imidazoline receptor; % inhibition: percent inhibition; i.t.: intrathecal; % MPE: percent maximum possible effect; μg: microgram; μOR: mu opioid receptor; MOR: morphine; MOX: moxonidine; ng: nanogram; nmol: nanomoles; OR: opioid receptor; pmol: picomoles; SP: substance P; S.D.: standard deviation; S.E.M.: standard error of the mean.

Animals:

Experimental subjects were 20–25 g male ICR mice (Harlan, Madison, Wis.) or 15–20 g male and female mice (gender-matched) with a C57BL/6 and 129/sv genetic background (designated B6,129). Subjects were housed in groups of five to ten in a temperature- and humidity-controlled environment. Subjects were maintained on a 12 hr light/dark cycle and had free access to food and water.

Chemicals:

Moxonidine hydrochloride (Solvay Pharmaceuticals GmbH, Hannover, Germany) was dissolved in an aqueous 1% by vol. acetic acid solution and diluted with acidified saline solution (pH 3.2–4.0). Substance P (Sigma, St. Louis, Mo.) was dissolved in acidified saline solution. Morphine sulfate and deltorphin II (from NIDA) were dissolved in 0.9% by wt. saline solution.

Substance P Nociceptive Test Procedure:

A constant dose of SP (15 ng) was injected intrathecally and the number of SP-elicited behaviors were counted for 1 minute. This dose of SP typically produces approximately 40–60 behaviours (scratches and bites directed to the hindlimbs) in the first minute after injection. Co-administration of opioid or adrenergic analgesics with SP dose-dependently inhibits those behaviours. Moxonidine, the OR agonists morphine or deltorphin II, or combinations of moxonidine with morphine or deltorphin II were co-administered with SP; % inhibition of SP-induced behavior was calculated according to the following equation:

$$\% \text{ Inhibition} = \frac{\text{Control} - \text{Experimental}}{\text{Control}} \times 100$$

The $ED_{50}$ is calculated as the dose that produces a 50% reduction of the number of SP-induced behavioral responses per minute.

Statistical (Isobolographic) Analysis:

Data describing antinociception are expressed as means of percent inhibition (% inhibition) with standard error of the mean (S.E.M.). The $ED_{50}$ values and confidence limits were calculated according to the method of Tallarida and Murray. Groups of greater than 7 animals were used for each dose. For each experiment, three dose-response curves were generated. These included dose response curves for agonist 1 (i.e., morphine or deltorphin), agonist 2 (i.e., moxonidine), and agonist 1 and 2 co-administered in an equal potency ratio. The results are summarized in Tables I and II.

To test for synergistic interactions, the $ED_{50}$ values and the 95% confidence intervals of all dose-response curves were arithmetically arranged around the $ED_{50}$ value using the equation $(\ln(10) \cdot ED_{50}) \cdot (\text{S.E.M. of log } ED_{50})$. Isobolographic analysis necessitates this manipulation. An additive $ED_{50}$ value would be derived from a dose-response curve where the interactions between morphine and moxonidine merely represent the sum of the effects of each drug when given alone. When testing an interaction between two drugs given in combination for synergy, additivity, or subadditivity, a theoretical additive $ED_{50}$ value is calculated for the combination based on the dose-response curves of each drug administered separately. This theoretical value is then compared by a t-test (p<0.05) with the observed experimental $ED_{50}$ value of the combination. These values are based on total dose of both drugs; in other words, the total dose of moxonidine plus the total dose of morphine. The observed and theoretical $ED_{50}$ values are presented in Tables I and II.

Synergistic Effect of Moxonidine and Morphine in ICR mice:

Intrathecally administered moxonidine ($ED_{50}$:110 pmol, 87–130) and morphine ($ED_{50}$:730 pmol, 400–1100) both inhibited SP-induced behaviour in ICR mice. Based on these $ED_{50}$ values, the morphine/moxonidine equi-effective dose-ratio was determined to be 10:1. When administered in combination, the $ED_{50}$ values of moxonidine ($ED_{50}$:12 pmol, 3–20) and morphine ($ED_{50}$:120 pmol, 78–160) are markedly lower than that of either agonist administered individually (Table I). This observation indicates an increase in potency for each drug administered in the presence of the other compared to each drug administered alone. Specifically, the potency of moxonidine increased 9.2-fold in the presence of morphine and likewise the potency of morphine increased 6.1-fold in the presence of moxonidine. The co-administration of moxonidine/morphine combinations in mice resulted in analgesic dose-response curves with $ED_{50}$ values significantly less than the calculated theoretical additive values (Table I). Isobolographic analysis revealed that the observed $ED_{50}$ value of the combination was significantly less than the calculated theoretical additive $ED_{50}$ value. This result proves a synergistic interaction between moxonidine and morphine.

Synergistic effect of Moxonidine and Deltorphin II:

Intrathecally administered moxonidine ($ED_{50}$:120 pmol, 93–140) and deltorphin II ($ED_{50}$:2100 pmol, 1710–2600) both inhibited SP-induced behaviour in ICR mice. Based on these $ED_{50}$ values, the deltorphin II/moxonidine equi-effective dose-ratio was determined to be 25:1. When administered in combination, the $ED_{50}$ values of moxonidine ($ED_{50}$:6.1 pmol, 3.1–9.1) and deltorphin II ($ED_{50}$:150 pmol, 79–230) were markedly lower than that of either agonist administered individually (Table II). This observation indicates an increase in potency for each drug administered in the presence of the other compared to each drug administered alone. Specifically, the potency of moxonidine increased 20-fold in the presence of deltorphin and likewise the potency of deltorphin increased 14-fold in the presence of moxonidine. The administration of moxonidine/deltorphin II-combinations in mice resulted in analgesic dose-response curves with $ED_{50}$ values significantly less than the calculated theoretical additive values (Table II). Isobolographic analysis revealed that the observed $ED_{50}$ value of the combination was signicantly less than the calculated theoretical additive $ED_{50}$ value. This result proves a synergistic interaction between moxonidine and deltorphin II.

TABLE I

Summary of Moxonidine/Morphine Spinal Analgesic Synergy in SP Test

| Probe, Drug (pmol per animal, i.t.) | $ED_{50}$ Morphine (95% C.L.) | $ED_{50}$ Moxonidine (95% C.L.) |
|---|---|---|
| Single Drug Morphine + Moxonidine (10:1 ratio): | 730 (400–1100) | 110 (87–130) |
| Observed Combination | 120 (78–160)* | 12 (3–20)* |
| Theoretical Additive | 360 (280–450)) | 36 (28–45) |

* = Significantly distinct from the calculated theoretical additive effect.

TABLE II

Summary of Moxonidine/Deltorphin Spinal Analgesic Synergy in SP Test

| Probe, Drug (pmol per animal, i.t.) | $ED_{50}$ Deltorphin (95% C.L.) | $ED_{50}$ Moxonidine (95% C.L.) |
|---|---|---|
| Single Drug Deltorphine + Moxonidine (25:1 ratio) | 2141 (1707–2574) | 115 (93–138) |
| Observed Combination | 152 (79–227)* | 6.1 (3.1–9.1)* |
| Theoretical Additive | 1228 (1050–1408) | 49 (42–56) |

* = Significantly distinct from the calculated theoretical additive effect.

The experiments demonstrate that the moxonidine, an $I_1/\alpha_2$ AR agonist, combined with the non-selective OR agonist morphine or the δOR-selective agonist deltorphin II produces spinal analgesic synergy in ICR mice. Thus, the resultant effect of the interaction of the combined two drugs, i.e., when administered together, is a greater-than-additive or multiplicative effect compared to each drug administered alone. The potency of morphine or deltorphin II administered in combination with moxonidine is significantly increased relative to that of each agonist administration alone.

Systemical Administration of Moxonidine and Morphine:

Systemically (intraperitoneally) administered moxonidine ($ED_{50}$:12 mg/kg, 10–15) and morphine ($ED_{50}$:9.7 mg/kg, 7.4–13) both inhibited SP-induced behaviour in B6,129 mice. Based on these $ED_{50}$ values, the morphine/moxonidine equi-effective dose-ratio was determined to be 1:1. When administered in combination, the $ED_{50}$ values of moxonidine ($ED_{50}$:2.1 mg/kg, 0.11–4.1) and morphine ($ED_{50}$:2.1 mg/kg, 0.11–4.1) were markedly lower than that of either agonist administered individually (Table III). This observation indicates an increase in potency for each drug administered in the presence of the other compared to each drug administered alone. Specifically, the potency of moxonidine increased approximately 5.7-fold in the presence of morphine and likewise the potency of morphine increased approximately 4.6-fold in the presence of moxonidine. The co-administration of moxonidine/morphine- combinations in mice resulted in analgesic dose-response curves with $ED_{50}$ values significantly less than the calculated theoretical additive values (Table III). Isobolographic analysis revealed that the observed $ED_{50}$ value of the combination was significantly less than the calculated theoretical additive $ED_{50}$ value. This result proves a synergistic interaction between moxonidine and morphine after systemic administration.

TABLE III

Summary of Moxonidine/Morphine Systemic Analgesic Synergy in SP Test

| Probe, Drug (mg/kg, i.p.) | $ED_{50}$ Morphine (95% C.L.) | $ED_{50}$ Moxonidine (95% C.L.) |
|---|---|---|
| Single Drug Morphine + Moxonidine (1:1 ratio) | 9.7 (7.4–13) | 12 (10–15) |
| Observed Combination | 2.1 (0.11–4.1)* | 2.1 (0.11–4.1)* |
| Theoretical Additive | 5.5 (3.5–7) | 5.5 (3.5–7) |

* = Significantly distinct from the calculated theoretical additive effect.

The experiments demonstrate that systemically (intraperitoneally) administered moxonidine, an $I_1/\alpha_2$ AR agonist, combined with the non-selective OR agonist morphine also produces analgesic synergy in B6,129 mice. Thus, the resultant effect of the interaction of the combined two drugs, i.e., when administered together, is a greater-than-additive or multiplicative effect compared to each drug administered alone. The potency of morphine systemically administered in combination with moxonidine is significantly increased relative to that of each agonist administration alone.

The combination of moxonidine and its acid-addition salts with opioid analgesic compounds like morphine and deltorphin are therefore suitable for the treatment and/or prophylaxis of severe pain in acute and chronic pain conditions. The doses to be administered may differ between individuals and naturally vary depending on the type of condition to be treated and the route of administration. For example, locally applicable formulations, in particular intrathecally injectable formulations, generally contain substantially less amount of active substance than systemically applicable, e.g. oral formulations. Continuous application may be needed for chronic pain conditions. For example, solutions containing 0.1 to 3 μg moxonidine, in particular 1 to 3 μg moxonidine, and 1 to 3.3 mg morphine, respectively, per single unit dosages are suitable for intrathecal injections. The solutions may be a single solution containing both compounds or separate solutions each containing one of the two compounds.

The following examples are intended as a more detailed illustration of the manufacture of a pharmaceutical preparation containing combinations of moxonidine and opioid analgesic compounds that are suitable for the treatment and/or prophylaxis of pain in humans, however, without limiting the scope of the application.

EXAMPLE 1

A liquid preparation containing moxonidine and morphine for intrathecal administration is composed of:

| | |
|---|---|
| Morphine sulphate: | 3.3 g |
| Moxonidine hydrochloride: | 3 mg |
| Isotonic aqueous saline solution: (for injection purposes) | quantum satis ad 1 l |

Moxonidine hydrochloride and morphine sulphate were dissolved in the saline solution. The resulting solution was filled into ampouls of 1 ml content under nitrogen and sterilised.

EXAMPLE 2

Kit for intrathecal pain relieving treatment:

Component A:

Moxonidine containing injection solution. A liquid preparation containing moxonidine is composed of:

| | |
|---|---|
| Moxonidine hydrochloride: | 3 mg |
| Isotonic aqueous saline solution: (for injection purposes) | quantum satis ad 1 l |

Moxonidine was dissolved in the saline solution. The resultant solution was filled into ampouls of 1 ml content under nitrogen and sterilised.

Component B:
Morphine sulphate containing injection solution.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A pharmaceutical analgesic composition, comprising synergistically analgesic effective amounts of:
   moxonidine or a pharmaceutically acceptable salt thereof; and
   an opioid analgesic agent selected from the group consisting of morphine and deltorphin or a pharmaceutically acceptable derivative or salt thereof.

2. A pharmaceutical analgesic composition according to claim 1 wherein said composition is an intrathecally injectable solution.

3. A method for producing analgesia in a larger mammal comprising:
   co-administering synergistically analgesic effective amounts of moxonidine or a pharmaceutically acceptable salt thereof and an opioid analgesic agent selected from the group consisting of morphine and deltorphin or a pharmaceutically acceptable derivative or salt thereof.

4. A method for producing analgesia in a mammal according to claim 3 wherein said co-administering is intrathecally.

5. A method for producing a pharmaceutical analgesic composition comprising combining synergistically analgesic effective amounts of:
   moxonidine or a pharmaceutically acceptable salt thereof; and
   an opioid analgesic agent selected from the group consisting of morphine and deltorphin or a pharmaceutically acceptable derivative or salt thereof.

6. A pharmaceutically analgesic composition in the form of an intrathecally injectable solution, comprising synergistically analgesic effective amounts of:
   0.1 to 3 mg moxonidine or a pharmaceutically acceptable salt thereof per single unit dosage; and
   1 to 3.3 mg of an opioid analgesic agent selected from the group consisting of morphine and deltorphin or a pharmaceutically acceptable derivative or salt thereof,
   wherein the moxonidine and opioid analgesic agent are in a single solution or in separate solutions.

* * * * *